(12) United States Patent
Cotton

(10) Patent No.: US 12,290,655 B2
(45) Date of Patent: May 6, 2025

(54) WOUND DRESSING

(71) Applicant: ConvaTec Limited, Deeside (GB)

(72) Inventor: Stephen Cotton, Nottingham (GB)

(73) Assignee: CONVATEC LIMITED, Flintshire (GB)

( * ) Notice: Subject to any disclaimer, the term of this patent is extended or adjusted under 35 U.S.C. 154(b) by 192 days.

(21) Appl. No.: 15/770,152

(22) PCT Filed: Oct. 21, 2016

(86) PCT No.: PCT/GB2016/053295
§ 371 (c)(1),
(2) Date: Apr. 20, 2018

(87) PCT Pub. No.: WO2017/068364
PCT Pub. Date: Apr. 27, 2017

(65) Prior Publication Data
US 2018/0311420 A1    Nov. 1, 2018

(30) Foreign Application Priority Data

Oct. 21, 2015   (GB) ...................................... 1518669

(51) Int. Cl.
| | | |
|---|---|---|
| A61M 39/08 | (2006.01) | |
| A61M 1/00 | (2006.01) | |
| A61M 39/10 | (2006.01) | |

(52) U.S. Cl.
CPC .............. *A61M 39/08* (2013.01); *A61M 1/84* (2021.05); *A61M 1/915* (2021.05); *A61M 2039/1038* (2013.01)

(58) Field of Classification Search
CPC .... A61M 1/008; A61M 1/0088; A61M 39/00; A61M 39/08; A61M 2039/1038;
(Continued)

(56) References Cited

U.S. PATENT DOCUMENTS 4,138,036 A *  2/1979  Bond .................... B65D 77/06
                                                    222/105
4,441,215 A *  4/1984  Kaster .................... A61F 2/064
                                                    623/1.53
(Continued)

FOREIGN PATENT DOCUMENTS

EP    2711034 A1    3/2014
EP    2817038 A1    12/2014
(Continued)

OTHER PUBLICATIONS

US 11,338,078 B2, 05/2022, Coulthard et al. (withdrawn)
(Continued)

*Primary Examiner* — Adam Marcetich
*Assistant Examiner* — Eric Rassavong
(74) *Attorney, Agent, or Firm* — Taft Stettinius & Hollister LLP; Ryan O. White; Derek B. Lavender

(57) ABSTRACT

A negative pressure wound therapy dressing comprising a drainage tube. The drainage tube comprises a tube knitted or braided from monofilament yarn and surrounded by an impermeable sheath. Also disclosed is a method of treating a wound using the negative pressure wound therapy dressing, and the knitted or braided tube for use in medical applications.

20 Claims, 2 Drawing Sheets

Figure 1:
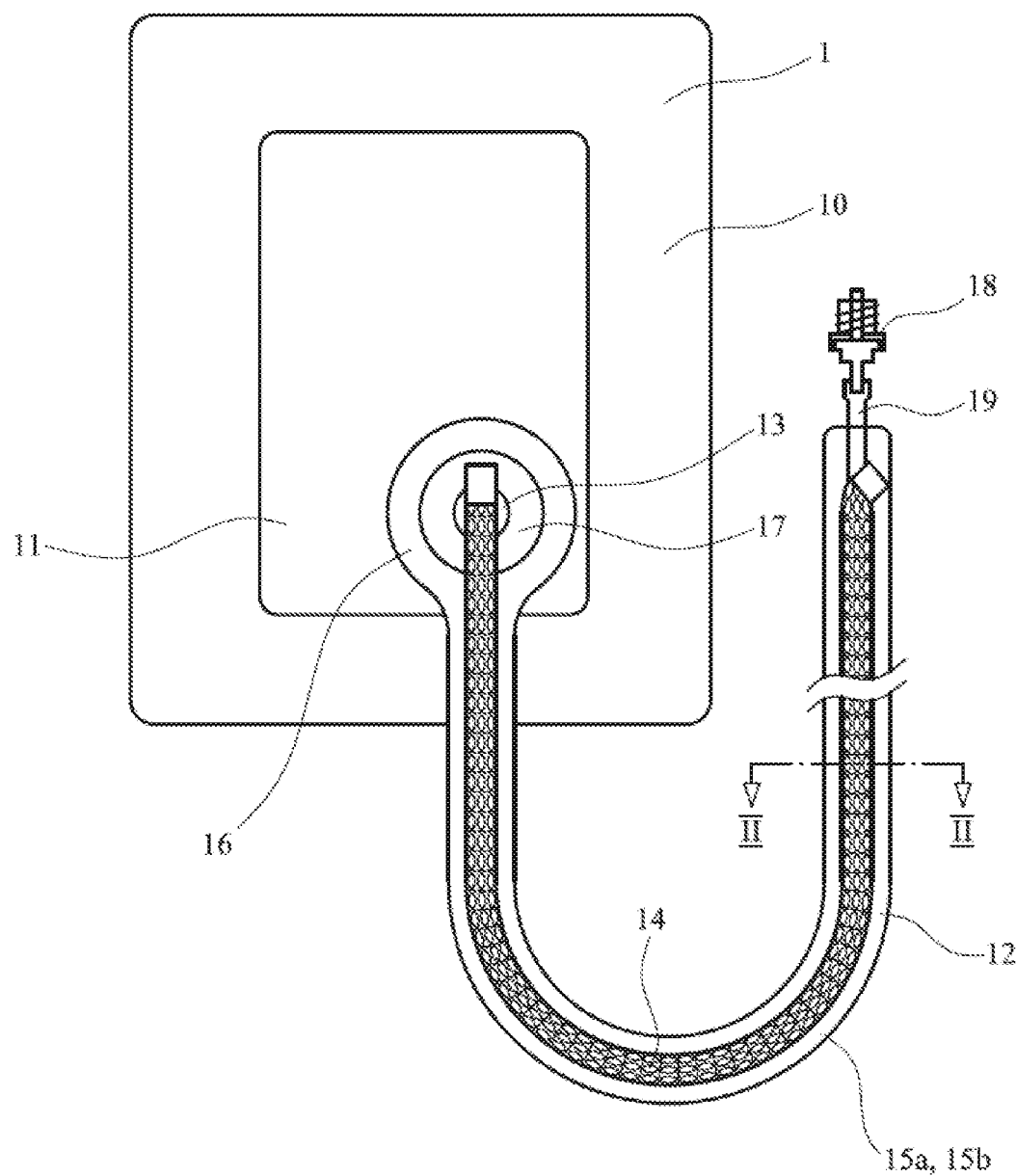

(58) Field of Classification Search
CPC .......... A61M 2039/0009; A61M 27/00; A61M 1/84; A61M 1/90; A61F 13/0216; A61F 13/00068; A61F 2013/00536; B65D 2231/004
See application file for complete search history.

(56) References Cited

U.S. PATENT DOCUMENTS

| | | | |
|---|---|---|---|
| 5,156,300 A * | 10/1992 | Spahni | B65D 83/0055 222/464.2 |
| 5,358,492 A * | 10/1994 | Feibus | A61M 27/00 604/355 |
| 5,630,855 A | 5/1997 | Lundbäck | |
| 5,957,974 A | 9/1999 | Thompson et al. | |
| 6,695,823 B1 | 2/2004 | Lina et al. | |
| 8,083,712 B2 | 12/2011 | Biggie et al. | |
| 8,308,714 B2 | 11/2012 | Weston et al. | |
| 8,439,894 B1 | 5/2013 | Miller | |
| 8,521,979 B2 | 8/2013 | Laberge et al. | |
| 8,814,840 B2 | 8/2014 | Evans et al. | |
| 8,858,516 B2 | 10/2014 | Hu et al. | |
| 9,205,183 B2 | 12/2015 | Hartwell et al. | |
| 10,016,537 B2 | 7/2018 | Menon et al. | |
| 10,046,096 B2 | 8/2018 | Askem et al. | |
| 10,076,447 B2 | 9/2018 | Barta et al. | |
| 10,076,587 B2 | 9/2018 | Locke et al. | |
| 10,143,784 B2 | 12/2018 | Walton et al. | |
| 10,426,670 B2 | 10/2019 | von Blucher et al. | |
| 10,426,747 B2 | 10/2019 | Johnson | |
| 10,426,874 B2 | 10/2019 | Chien et al. | |
| 10,426,875 B2 | 10/2019 | Blott et al. | |
| 10,426,938 B2 | 10/2019 | Locke et al. | |
| 10,434,015 B2 | 10/2019 | Taylor et al. | |
| 10,434,142 B2 | 10/2019 | Niazi et al. | |
| 10,434,210 B2 | 10/2019 | Olson et al. | |
| 10,434,284 B2 | 10/2019 | Hanson et al. | |
| 10,449,094 B2 | 10/2019 | Donda et al. | |
| D866,756 S | 11/2019 | Allen et al. | |
| 10,463,760 B2 | 11/2019 | Karthikeyan et al. | |
| 10,463,773 B2 | 11/2019 | Haggstrom et al. | |
| 10,470,933 B2 | 11/2019 | Riesinger | |
| 10,470,936 B2 | 11/2019 | Wohlgemuth et al. | |
| 10,471,122 B2 | 11/2019 | Shi et al. | |
| 10,471,190 B2 | 11/2019 | Locke et al. | |
| 10,478,345 B2 | 11/2019 | Barta et al. | |
| 10,478,346 B2 | 11/2019 | Knutson | |
| 10,478,394 B2 | 11/2019 | Yu | |
| 10,485,707 B2 | 11/2019 | Sexton | |
| 10,485,891 B2 | 11/2019 | Andrews et al. | |
| 10,485,892 B2 | 11/2019 | Hands et al. | |
| 10,485,906 B2 | 11/2019 | Freedman et al. | |
| 10,486,135 B2 | 11/2019 | Yang et al. | |
| 10,492,956 B2 | 12/2019 | Zamierowski | |
| 10,493,178 B2 | 12/2019 | Marchant et al. | |
| 10,493,184 B2 | 12/2019 | Collinson et al. | |
| 10,493,185 B2 | 12/2019 | Stokes et al. | |
| 10,500,099 B2 | 12/2019 | Hung et al. | |
| 10,500,103 B2 | 12/2019 | Croizat et al. | |
| 10,500,104 B2 | 12/2019 | Sookraj | |
| 10,500,173 B2 | 12/2019 | Yang et al. | |
| 10,500,235 B2 | 12/2019 | Wardell | |
| 10,500,300 B2 | 12/2019 | Dybe et al. | |
| 10,500,301 B2 | 12/2019 | Laurensou | |
| 10,500,302 B2 | 12/2019 | Holm et al. | |
| 10,501,487 B2 | 12/2019 | Andrews et al. | |
| 10,506,928 B2 | 12/2019 | Locke et al. | |
| 10,507,141 B2 | 12/2019 | Allen et al. | |
| 10,507,259 B2 | 12/2019 | Cree et al. | |
| 10,512,707 B2 | 12/2019 | Whalen, III et al. | |
| 10,525,170 B2 | 1/2020 | Havenstrite et al. | |
| 10,532,137 B2 | 1/2020 | Pratt et al. | |
| 10,532,194 B2 | 1/2020 | Locke et al. | |
| 10,537,657 B2 | 1/2020 | Phillips et al. | |
| 10,542,936 B2 | 1/2020 | Goldberg et al. | |
| 10,543,133 B2 | 1/2020 | Shaw et al. | |
| 10,543,293 B2 | 1/2020 | Suschek | |
| 10,548,777 B2 | 2/2020 | Locke et al. | |
| 10,549,008 B2 | 2/2020 | Yoo | |
| 10,549,016 B2 | 2/2020 | Bushko et al. | |
| 10,549,017 B2 | 2/2020 | Hsiao et al. | |
| 10,555,838 B2 | 2/2020 | Wu et al. | |
| 10,555,839 B2 | 2/2020 | Hartwell | |
| 10,556,044 B2 | 2/2020 | Robinson et al. | |
| 10,561,533 B2 | 2/2020 | Hoggarth et al. | |
| 10,561,536 B2 | 2/2020 | Holm et al. | |
| 10,568,767 B2 | 2/2020 | Addison et al. | |
| 10,568,768 B2 | 2/2020 | Long et al. | |
| 10,568,770 B2 | 2/2020 | Robinson et al. | |
| 10,568,771 B2 | 2/2020 | MacDonald et al. | |
| 10,568,773 B2 | 2/2020 | Tuck et al. | |
| 10,568,983 B2 | 2/2020 | Gerdes et al. | |
| 10,575,991 B2 | 3/2020 | Dunn | |
| 10,575,992 B2 | 3/2020 | Sarangapani et al. | |
| 10,576,037 B2 | 3/2020 | Harrell | |
| 10,576,189 B2 | 3/2020 | Locke et al. | |
| 10,583,042 B2 | 3/2020 | Sarangapani et al. | |
| 10,583,228 B2 | 3/2020 | Shuler et al. | |
| 10,589,007 B2 | 3/2020 | Coulthard et al. | |
| 10,590,184 B2 | 3/2020 | Kuo | |
| 10,610,414 B2 | 4/2020 | Hartwell et al. | |
| 10,610,415 B2 | 4/2020 | Griffey et al. | |
| 10,610,623 B2 | 4/2020 | Robinson et al. | |
| 10,617,569 B2 | 4/2020 | Bonn | |
| 10,617,608 B2 | 4/2020 | Shin et al. | |
| 10,617,769 B2 | 4/2020 | Huang | |
| 10,617,784 B2 | 4/2020 | Yu et al. | |
| 10,617,786 B2 | 4/2020 | Kluge et al. | |
| 10,618,266 B2 | 4/2020 | Wright et al. | |
| 10,624,984 B2 | 4/2020 | Courage et al. | |
| 10,625,002 B2 | 4/2020 | Locke et al. | |
| 10,632,019 B2 | 4/2020 | Vitaris | |
| 10,632,224 B2 | 4/2020 | Hardy et al. | |
| 10,639,206 B2 | 5/2020 | Hu et al. | |
| 10,639,350 B2 | 5/2020 | Arber et al. | |
| 10,639,404 B2 | 5/2020 | Lichtenstein | |
| 10,646,614 B2 | 5/2020 | Grinstaff et al. | |
| 10,653,562 B2 | 5/2020 | Robinson et al. | |
| 10,653,782 B2 | 5/2020 | Ameer et al. | |
| 10,653,810 B2 | 5/2020 | Datt et al. | |
| 10,653,821 B2 | 5/2020 | Nichols | |
| 10,653,823 B2 | 5/2020 | Bharti et al. | |
| 10,660,799 B2 | 5/2020 | Wu et al. | |
| 10,660,851 B2 | 5/2020 | Millis et al. | |
| 10,660,992 B2 | 5/2020 | Canner et al. | |
| 10,660,994 B2 | 5/2020 | Askem et al. | |
| 10,667,955 B2 | 6/2020 | Allen et al. | |
| 10,667,956 B2 | 6/2020 | Van Holten et al. | |
| 10,682,257 B2 | 6/2020 | Lu | |
| 10,682,258 B2 | 6/2020 | Manwaring et al. | |
| 10,682,259 B2 | 6/2020 | Hunt et al. | |
| 10,682,318 B2 | 6/2020 | Twomey et al. | |
| 10,682,386 B2 | 6/2020 | Ellis-Behnke et al. | |
| 10,682,446 B2 | 6/2020 | Askem et al. | |
| 10,687,983 B2 | 6/2020 | Dahlberg et al. | |
| 10,687,985 B2 | 6/2020 | Lee et al. | |
| 10,688,215 B2 | 6/2020 | Munro et al. | |
| 10,688,217 B2 | 6/2020 | Hanson et al. | |
| RE48,117 E | 7/2020 | Albert et al. | |
| 10,702,419 B2 | 7/2020 | Locke et al. | |
| 10,702,420 B2 | 7/2020 | Hammond et al. | |
| 10,703,942 B2 | 7/2020 | Tunius | |
| 10,709,760 B2 | 7/2020 | Gronberg et al. | |
| 10,709,807 B2 | 7/2020 | Kshirsagar | |
| 10,709,883 B2 | 7/2020 | Spector | |
| 10,716,711 B2 | 7/2020 | Locke et al. | |
| 10,716,874 B2 | 7/2020 | Koyama et al. | |
| 10,729,589 B2 | 8/2020 | Dorian et al. | |
| 10,729,590 B2 | 8/2020 | Simmons et al. | |
| 10,736,787 B2 | 8/2020 | Hannigan et al. | |
| 10,736,788 B2 | 8/2020 | Locke et al. | |
| 10,736,985 B2 | 8/2020 | Odermatt et al. | |
| 10,737,003 B2 | 8/2020 | Fujisaki | |
| 10,743,900 B2 | 8/2020 | Ingram et al. | |
| 10,744,040 B2 | 8/2020 | Kazala, Jr. et al. | |

(56) References Cited

U.S. PATENT DOCUMENTS

| | | |
|---|---|---|
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 11,058,587 B2 | 7/2021 | Adie et al. |
| 11,058,588 B2 | 7/2021 | Albert et al. |
| 11,076,997 B2 | 8/2021 | Hunt et al. |
| 11,090,195 B2 | 8/2021 | Adie et al. |
| 11,090,196 B2 | 8/2021 | Gowans et al. |
| 11,090,409 B2 | 8/2021 | Zimnitsky et al. |
| 11,096,830 B2 | 8/2021 | Pratt et al. |
| 11,116,669 B2 | 9/2021 | Gowans et al. |
| 11,123,474 B2 | 9/2021 | Hartwell |
| 11,141,521 B2 | 10/2021 | Beadle et al. |
| 11,154,649 B2 | 10/2021 | Collinson et al. |
| 11,191,887 B2 | 12/2021 | Locke et al. |
| 11,246,757 B2 | 2/2022 | Hartwell et al. |
| 11,247,034 B2 | 2/2022 | Armstrong et al. |
| 11,253,399 B2 | 2/2022 | Hall et al. |
| 11,273,077 B2 | 3/2022 | Kubek |
| 11,291,587 B2 | 4/2022 | Kilpadi |
| 11,364,150 B2 | 6/2022 | Gowans et al. |
| 11,400,204 B2 | 8/2022 | Coulthard et al. |
| 11,413,389 B2 | 8/2022 | Locke et al. |
| 11,419,767 B2 | 8/2022 | Dunn et al. |
| 11,439,741 B2 | 9/2022 | Hartwell |
| 11,771,796 B2 | 10/2023 | Collinson et al. |
| 11,801,164 B2 | 10/2023 | Hartwell et al. |
| 11,801,338 B2 | 10/2023 | Collinson et al. |
| 11,813,394 B2 | 11/2023 | Joshi et al. |
| 11,864,981 B2 | 1/2024 | Allen et al. |
| 11,896,733 B2 | 2/2024 | Zimnitsky et al. |
| 11,903,798 B2 | 2/2024 | Askem et al. |
| 11,931,226 B2 | 3/2024 | Collinson et al. |
| 11,950,984 B2 | 4/2024 | Pratt et al. |
| 11,974,902 B2 | 5/2024 | Greener |
| 12,004,925 B2 | 6/2024 | Hartwell |
| 2002/0177800 A1* | 11/2002 | Bagaoisan ........ A61M 25/0068 604/6.12 |
| 2004/0087885 A1 | 5/2004 | Kawano et al. |
| 2006/0155260 A1 | 7/2006 | Blott et al. |
| 2006/0172000 A1 | 8/2006 | Cullen et al. |
| 2007/0185426 A1 | 8/2007 | Ambrosio et al. |
| 2007/0208300 A1* | 9/2007 | Pravong ................ F16L 11/15 604/525 |
| 2007/0219512 A1 | 9/2007 | Heaton et al. |
| 2007/0239078 A1 | 10/2007 | Jaeb |
| 2009/0082731 A1* | 3/2009 | Moreno ............ A61B 17/3439 604/527 |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0036333 A1 | 2/2010 | Schenk, III et al. |
| 2010/0069863 A1 | 3/2010 | Olson |
| 2010/0125233 A1 | 5/2010 | Edward S. et al. |
| 2010/0125258 A1 | 5/2010 | Coulthard et al. |
| 2010/0137775 A1 | 6/2010 | Hu et al. |
| 2010/0185163 A1 | 7/2010 | Heagle |
| 2010/0298790 A1 | 11/2010 | Guidi et al. |
| 2010/0318043 A1 | 12/2010 | Malhi et al. |
| 2010/0324516 A1* | 12/2010 | Braga ................ A61F 13/00 604/378 |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0152799 A1 | 6/2011 | Kevin et al. |
| 2011/0172616 A1 | 7/2011 | Hartwell et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2011/0276016 A1 | 11/2011 | Tsai |
| 2012/0016322 A1 | 1/2012 | Coulthard et al. |
| 2012/0065602 A1 | 3/2012 | Adams et al. |
| 2012/0071845 A1 | 3/2012 | Hu et al. |
| 2012/0100538 A1 | 4/2012 | Mikolajczyk et al. |
| 2012/0130332 A1 | 5/2012 | Cotton et al. |
| 2012/0136325 A1 | 5/2012 | Allen et al. |
| 2012/0197237 A1* | 8/2012 | Holzbauer ........ A61M 25/0045 604/540 |
| 2012/0209226 A1 | 8/2012 | Simmons et al. |
| 2013/0053795 A1 | 2/2013 | Coulthard et al. |
| 2013/0123728 A1 | 5/2013 | Pratt et al. |
| 2013/0226063 A1 | 8/2013 | Taylor et al. |
| 2013/0267918 A1 | 10/2013 | Pan et al. |
| 2013/0296816 A1 | 11/2013 | Greener |
| 2014/0005618 A1 | 1/2014 | Locke et al. |
| 2014/0031771 A1 | 1/2014 | Locke et al. |
| 2014/0074053 A1 | 3/2014 | Locke et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276489 A1 | 9/2014 | Robinson et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2014/0336602 A1 | 11/2014 | Karpowicz et al. |
| 2014/0343519 A1 | 11/2014 | Weston |
| 2015/0018433 A1 | 1/2015 | Leipzig et al. |
| 2015/0057624 A1 | 2/2015 | Simmons et al. |
| 2015/0057625 A1 | 2/2015 | Coulthard |
| 2015/0071985 A1 | 3/2015 | Walker et al. |
| 2015/0073359 A1 | 3/2015 | Hudspeth et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1* | 5/2015 | Allen ................ A61F 13/00068 604/319 |
| 2015/0148785 A1 | 5/2015 | Kleiner |
| 2015/0174304 A1 | 6/2015 | Askem et al. |
| 2015/0182677 A1 | 7/2015 | Collinson et al. |
| 2015/0245949 A1 | 9/2015 | Locke et al. |
| 2015/0246164 A1 | 9/2015 | Heaton et al. |

(56) References Cited

U.S. PATENT DOCUMENTS

| | | |
|---|---|---|
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0290364 A1 | 10/2015 | Wall et al. |
| 2015/0320901 A1 | 11/2015 | Chandrashekhar-Bhat et al. |
| 2015/0351970 A1 | 12/2015 | Dagger et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0151547 A1 | 6/2016 | Hartwell et al. |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140753 A1* | 5/2018 | Askem ............... A61M 1/985 |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336345 A1 | 11/2019 | Bannwart |
| 2019/0336346 A1 | 11/2019 | Locke et al. |
| 2019/0336640 A1 | 11/2019 | Msmara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350765 A1 | 11/2019 | Heagle et al. |
| 2019/0350970 A1 | 11/2019 | Saphier et al. |
| 2019/0351092 A1 | 11/2019 | Silver et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | MacPhee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | MacPhee et al. |
| 2019/0388589 A1 | 12/2019 | MacPhee et al. |
| 2020/0000955 A1 | 1/2020 | Andrews et al. |
| 2020/0000960 A1 | 1/2020 | Kellar et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0030153 A1 | 1/2020 | Johannison et al. |
| 2020/0030480 A1 | 1/2020 | Choi |
| 2020/0030499 A1 | 1/2020 | Menon et al. |

(56) References Cited

U.S. PATENT DOCUMENTS

| | | |
|---|---|---|
| 2020/0038023 A1 | 2/2020 | Dunn |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046568 A1 | 2/2020 | Sexton |
| 2020/0046663 A1 | 2/2020 | Murdock et al. |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0061254 A1 | 2/2020 | Joshi et al. |
| 2020/0069477 A1 | 3/2020 | Holm et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085991 A1 | 3/2020 | Coomber |
| 2020/0085992 A1 | 3/2020 | Locke et al. |
| 2020/0086049 A1 | 3/2020 | Park et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0107964 A1 | 4/2020 | Locke et al. |
| 2020/0107965 A1 | 4/2020 | Greener |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121510 A1 | 4/2020 | Hartwell et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0155355 A1 | 5/2020 | Hill et al. |
| 2020/0155358 A1 | 5/2020 | Wheldrake |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179558 A1 | 6/2020 | Munro et al. |
| 2020/0179673 A1 | 6/2020 | Wan |
| 2020/0188180 A1 | 6/2020 | Akbari et al. |
| 2020/0188182 A1 | 6/2020 | Sanders et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0237564 A1 | 7/2020 | Hammond et al. |
| 2020/0237816 A1 | 7/2020 | Lait |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289328 A1 | 9/2020 | Luckemeyer et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306094 A1 | 10/2020 | Kushnir et al. |
| 2020/0315853 A1 | 10/2020 | Waite |
| 2020/0315854 A1 | 10/2020 | Simmons et al. |
| 2020/0316271 A1 | 10/2020 | Lin |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |
| 2021/0187171 A1 | 6/2021 | Collinson et al. |
| 2021/0228417 A1 | 7/2021 | Ha et al. |
| 2021/0322666 A1 | 10/2021 | Greener |
| 2021/0338488 A1 | 11/2021 | Pratt et al. |
| 2021/0338885 A1 | 11/2021 | Zimnitsky et al. |
| 2021/0353472 A1 | 11/2021 | Allen et al. |
| 2021/0361820 A1 | 11/2021 | Bourdillon et al. |
| 2021/0361854 A1 | 11/2021 | Askem et al. |
| 2021/0378872 A1 | 12/2021 | Gowans et al. |
| 2021/0379273 A1 | 12/2021 | Locke et al. |
| 2021/0401628 A1 | 12/2021 | Gowans et al. |
| 2021/0402049 A1 | 12/2021 | Waite et al. |

(56) References Cited

U.S. PATENT DOCUMENTS

| | | |
|---|---|---|
| 2022/0000670 A1 | 1/2022 | Adie et al. |
| 2022/0016332 A1 | 1/2022 | Joshi et al. |
| 2022/0023527 A1 | 1/2022 | Beadle et al. |
| 2022/0031231 A1 | 2/2022 | Hunt et al. |
| 2022/0031520 A1 | 2/2022 | Kilpadi |
| 2022/0047797 A1 | 2/2022 | Locke et al. |
| 2022/0072215 A1 | 3/2022 | Hartwell |
| 2022/0080105 A1 | 3/2022 | Askem et al. |
| 2022/0096727 A1 | 3/2022 | Collinson et al. |
| 2022/0117794 A1 | 4/2022 | Hartwell et al. |
| 2022/0117795 A1 | 4/2022 | Adie et al. |
| 2022/0117796 A1 | 4/2022 | Adie et al. |
| 2022/0117797 A1 | 4/2022 | Adie et al. |
| 2022/0183894 A1 | 6/2022 | Mumby et al. |
| 2022/0192886 A1 | 6/2022 | Hartwell et al. |
| 2022/0218528 A1 | 7/2022 | Askem et al. |
| 2022/0241113 A1 | 8/2022 | Hall et al. |
| 2022/0280713 A1 | 9/2022 | Collinson et al. |
| 2022/0313893 A1 | 10/2022 | Hartwell et al. |
| 2022/0347018 A1 | 11/2022 | Collinson et al. |
| 2023/0310221 A1 | 10/2023 | Allen et al. |
| 2023/0330321 A1 | 10/2023 | Adie et al. |
| 2023/0338196 A1 | 10/2023 | Greener |
| 2023/0338650 A1 | 10/2023 | Allen et al. |
| 2024/0009372 A1 | 1/2024 | Braga et al. |
| 2024/0099894 A1 | 3/2024 | Hartwell et al. |
| 2024/0139035 A1 | 5/2024 | Collinson et al. |
| 2024/0156645 A1 | 5/2024 | Braga et al. |
| 2024/0207102 A1 | 6/2024 | Allen et al. |

FOREIGN PATENT DOCUMENTS

| | | |
|---|---|---|
| EP | 3187204 A1 | 7/2017 |
| EP | 3848009 A1 | 7/2021 |
| EP | 3630031 B1 | 9/2021 |
| EP | 3434237 B1 | 11/2021 |
| EP | 3628289 B1 | 11/2021 |
| EP | 3096728 B1 | 12/2021 |
| EP | 3448451 B1 | 12/2021 |
| EP | 3681452 B1 | 12/2021 |
| EP | 3672655 B1 | 1/2022 |
| EP | 3964185 A1 | 3/2022 |
| EP | 3406231 B1 | 4/2022 |
| EP | 3586805 B1 | 4/2022 |
| EP | 3315145 B1 | 6/2022 |
| EP | 3703633 B1 | 6/2022 |
| EP | 4008299 A1 | 6/2022 |
| EP | 4023197 A1 | 7/2022 |
| EP | 3831350 B1 | 11/2022 |
| EP | 3096725 B1 | 10/2023 |
| EP | 3520830 B1 | 10/2023 |
| EP | 3328310 B1 | 11/2023 |
| EP | 3622976 B1 | 11/2023 |
| EP | 3666237 B1 | 11/2023 |
| EP | 3677291 B1 | 1/2024 |
| EP | 3769791 B1 | 1/2024 |
| EP | 3292878 B1 | 5/2024 |
| JP | 10305050 A | 11/1998 |
| JP | 2002200176 A | 7/2002 |
| JP | 2002210020 A | 7/2002 |
| JP | 2003520082 A | 7/2003 |
| JP | 2003275228 A | 9/2003 |
| JP | 2006523515 A | 10/2006 |
| JP | 2012530539 A | 12/2012 |
| JP | 2015520647 A | 7/2015 |
| WO | 2001052617 A2 | 7/2001 |
| WO | 2001070305 A1 | 9/2001 |
| WO | 2004093966 A1 | 11/2004 |
| WO | 2005018543 A2 | 3/2005 |
| WO | 2009002260 A1 | 12/2008 |
| WO | WO-2009106895 A1 | 9/2009 |
| WO | 2010147592 A1 | 12/2010 |
| WO | 2011087871 A2 | 7/2011 |
| WO | 2011121394 A1 | 10/2011 |
| WO | 2011135284 A1 | 11/2011 |
| WO | 2011144888 A1 | 11/2011 |
| WO | WO-2012057881 A1 | 5/2012 |
| WO | 2013015827 A2 | 1/2013 |
| WO | 2013126049 A1 | 8/2013 |
| WO | 2013175306 A2 | 11/2013 |
| WO | 2014014842 A1 | 1/2014 |
| WO | WO-2015052219 A1 | 4/2015 |
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | WO-2017068364 A1 | 4/2017 |
| WO | 2017125250 A1 | 7/2017 |
| WO | WO-2017196888 A1 | 11/2017 |
| WO | WO-2018009873 A1 | 1/2018 |
| WO | WO-2018009879 A1 | 1/2018 |
| WO | WO-2018009880 A1 | 1/2018 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |

OTHER PUBLICATIONS

International Patent Application No. PCT/US2017/041221 International Search Report and Written Opinion dated Sep. 13, 2017.
PCT/US2017/041208 International Preliminary Report on Patentability dated Jan. 8, 2019.
PCT/US2017/041216 International Preliminary Report on Patentability dated Jan. 8, 2019.
PCT/US2017/041221 International Preliminary Report on Patentability dated Jan. 8, 2019.
PCT/US2017/031817 International Preliminary Report on Patentability dated Nov. 13, 2018.
Colombian Application No. NC2018/0005230 Office Action dated May 31, 2018.
Great Britain Application No. GB1608099.6 search report dated Oct. 11, 2016.
PCT/GB2016/053295 International Preliminary Report on Patentability dated Apr. 24, 2018.
PCT/GB2016/053295 International Search Report and Written Opinion dated Jan. 17, 2017.
PCT/US2017/031817 International Search Report and Written Opinion dated Aug. 11, 2017.

(56) References Cited

OTHER PUBLICATIONS

PCT/US2017/041208 International Search Report and Written Opinion dated Sep. 8, 2017.
PCT/US2017/041216 International Search Report and Written Opinion dated Sep. 13, 2017.
PCT/US2017/041221 International Search Report and Written Opinion dated Sep. 13, 2017.
Examination Report Under Section 18(3); Intellectual Property Office of Great Britain; Great Britain Patent Application No. GB1518669.5; Apr. 1, 2020; 2 pages.
EP Examination Report for Application No. 16 787 539.2, dated Nov. 26, 2019, 10 pages.
Japanese Office Action; Japanese Patent Application No. 2018-520573; Oct. 27, 2020; 7 pages.
Office Action Summary; Japanese Patent Office; Japanese Patent Application No. 2018-520573; Jul. 6, 2021; 8 pages.
Communication of a notice of opposition; European Patent Office; European Patent Application No. 16787539.2; Sep. 1, 2021; 19 pages.
Canadian Office Action; Canadian Intellectual Property Office; Canadian Patent Application No. 3,002,616; Jan. 23, 2023; 4 pages.

\* cited by examiner

WOUND DRESSING

CROSS-REFERENCE

This application is a U.S. National Phase of International Application No. PCT/GB2016/053295, filed on Oct. 21, 2016, which claims the benefit of priority of GB 1518669.5, filed on Oct. 21, 2015, each of which is incorporated herein by reference in their entirety.

This invention relates generally wound dressings comprising drainage tubes, particularly for use during negative pressure wound therapy, and more specifically to drainage tubes suitable for use in such dressings or other applications.

Negative pressure wound therapy (NPWT) involves the application of a pressure that is reduced relative to that of the surroundings (commonly referred to as "negative pressure") to a wound, which causes mechanical contraction of the wound and removal of wound fluid, thus promoting formation of granulation tissue and accelerating wound closure. The technique is particularly effective in the treatment of slow healing wounds such as chronic leg ulcers and large open wounds. A dressing consisting of an occlusive drape, traversed by a drainage tube, is applied to the wound opening, forming a seal under which a negative pressure can be established. The drainage tube is connected to a negative pressure source allowing the wound fluid to be drawn away.

The drainage tube is conventionally a simple plastic tube. Such tubes are relatively inflexible, do not recover well from kinks and also can cause problems if the patient lies on them; for example, lying on the tubes can lead to pressure sores.

This invention provides a new form of drainage tube suitable for use in a negative pressure wound therapy dressing, which overcomes or substantially mitigates the above-mentioned and/or other limitations of the prior art.

In the first aspect of the invention, there is provided a negative pressure wound therapy dressing comprising a drainage tube, wherein the drainage tube comprises a tube knitted or braided from monofilament yarn and surrounded by an impermeable sheath.

The use of a knitted or braided monofilament to form the tube is advantageous as the resulting tube is flexible. It is also resilient and therefore springs back into shape very readily, but also flattens when pressure is applied to it. This means that there is less likelihood of a patient developing a pressure sore if they accidentally lie on the tube. In addition, a monofilament yarn does not have any fibres which may be shed into the drainage tube or dressing.

By a monofilament yarn is meant a yarn made from a single fibre, usually an extruded plastics material.

By a knitted tube is meant a tube of material formed by a circular knitting process, in which multiple loops of the yarn are interlocked.

By a braided tube is meant a tube of material formed by interlacing a number of yarns in a zigzag fashion through one another, to form the tube.

Preferably the tube is knitted from monofilament yarn. Such a tube is particularly resilient and springs back to its tubular shape very readily after being deformed.

The monofilament yarn may be of any material conventionally used to produce such yarns. Examples include polyester, polyamide, polyethylene, polypropylene and polybutylene terephthalate.

Preferably the tube has an external diameter of between 4 and 10 mm, more preferably between 5 and 8 mm and most preferably about 6 mm. A tube of such diameter is of a suitable size to act as a drainage tube without clogging but remains resiliently deformable.

The impermeable sheath may have any suitable form. For instance, the sheath may be an impermeable coating applied to the exterior of the knitted or braided tube. More preferably, however, the sheath is formed of one or more sheets of an impermeable material that surround the knitted or braided tube. For instance, the impermeable material may be formed of two sheets of an impermeable material that are sealed together at each side such that the tube is held between the sheets.

The sheets may be adhered to both the tube and to each other or alternatively only to each other on each side of the tube. Preferably the sheets are adhered to both the tube and to each other. This arrangement holds the tube in place between the sheets and prevents movement of the tube independently from the sheets.

The impermeable material may be adhered to itself and the tube by any suitable method, but preferably the impermeable material is heat-sealed to the tube and itself. Heat-sealing is advantageous because no additional components are introduced, such as an adhesive, which could contaminate the wound dressing.

The impermeable material may be any suitable material but preferably the impermeable material is a sheet of plastics material, and most preferably the impermeable material is polyurethane.

In general, one end of the knitted or braided tube will be connected to the body of the negative pressure therapy wound dressing, and the other end will be attached to a connector, by which the dressing may be coupled to a source of reduced pressure.

At the point at which the tube is connected to the body of the dressing, the tube may terminate adjacent to an opening in the occlusive backing layer of the dressing. Where the impermeable sheath comprises one or more sheets of impermeable material that surround the tube, one or more of those sheets may be formed into a tab that overlies the end of the tube and can be bonded to the backing layer of the dressing. The tab may be any suitable shape but preferably the tab is circular. By forming a tab in this manner, a large surface area is provided by which the tube may be attached to the dressing.

The open structure of the knitted or braided tube means that if the terminal portion of the tube is positioned over the opening in the backing layer of the dressing, reduced pressure may be applied to the dressing, in use, through the material of the tube. Wound exudate may pass through the material of the tube and be drawn away through the drainage tube. However, the knitted or braided material may also act as a filter, preventing or reducing the extent to which relatively large pieces of material that might cause an obstruction in the tube can be drawn from the wound dressing into the tube.

The other end of the drainage tube is adapted for connection to a source of negative pressure. A suitable connection may be achieved by a conventional connector with a plastics tube, eg of silicone or polyvinylchloride, that is inserted into the end of the knitted or braided tube. Again, the sheet(s) of impermeable material that surround the knitted or braided tube may extend to surround also the plastics tube of the connector in order to form an airtight seal between the connector and the knitted or braided tube.

The body of the wound dressing may be generally conventional and of similar form to other wound dressings for use in negative pressure wound therapy. For example, the dressing may comprise wound packing elements and absorbent components to aid in removal of exudate from the wound and to prevent a large wound from collapsing. As described above, the wound dressing will normally include a backing layer that is impermeable to air and liquid, so that in use a negative (reduced) pressure can be established between the dressing and the wound to which it is applied. It should be understood, however, that the backing layer may, and preferably does, have a low degree of permeability, to allow for the transmission of moisture vapour. Typically, the backing layer is a sheet of microporous plastics material, eg of polyurethane. The dressing will also generally have a wound contact layer or border that carries adhesive to fasten the dressing to a patient's skin and to form an airtight seal that permits the reduced pressure to be established beneath the dressing. The adhesive is most preferably a non-adherent or low-adherence adhesive, most preferably a soft silicone gel.

Apart from its use in negative pressure wound therapy dressings, the drainage tube of the form described above may find application in other medical devices where a flexible tube is required, especially where it is a requirement that the tube should be readily collapsible, for instance if a patient lies upon the tube, yet should return to its normal configuration after deformation. Hence, in a second aspect of the invention, there is provided a knitted or braided tube for use in medical applications, wherein the tube is knitted or braided from monofilament yarn and is surrounded by an impermeable sheath.

The tube may be of use in any suitable medical application, for example as, or as part of, a surgical drain such as a chest drain.

It will be appreciated that the knitted or braided tube may have any of the features discussed above in relation to the drainage tube of the negative pressure wound dressing of the first aspect of the invention.

The negative pressure wound therapy dressing comprising a drainage tube according to the first aspect of the invention may be used to treat a wound. Thus according to a third aspect of the invention there is provided a method of treating a wound comprising the steps of (a) applying a negative pressure wound therapy dressing according to the first aspect of the invention to a wound and (b) applying a reduced pressure to the dressing via the drainage tube.

It will be appreciated that the negative pressure wound dressing may have any of the features discussed above in relation to the first aspect of the invention.

Figure 2:
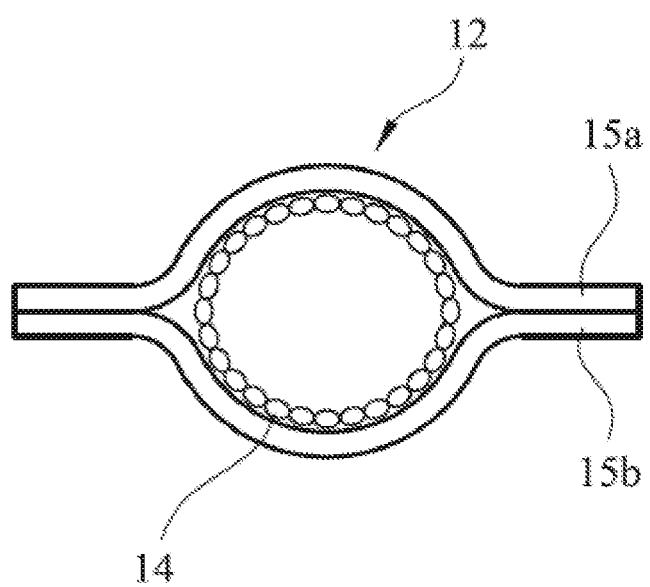

An embodiment of the invention will now be described in greater detail, by way of illustration only, with reference to the accompanying drawings, in which FIG. 1 is a plan view of a dressing according to the invention;

FIG. 2 is a cross-sectional view of a drainage tube forming part of the dressing of FIG. 1, along line II-II in FIG. 1.

Referring first to FIG. 1, a wound dressing according to the invention comprises a generally rectangular dressing body 1 and a drainage tube 12.

The dressing body 1 comprises a backing layer 10 that constitutes the top (ie non-skin facing) surface of the dressing body 1, an adhesive skin contact layer that constitutes the underside of the dressing body and is consequently not visible in FIG. 1, and that, prior to use, is covered by a release liner (also not visible), and an absorbent body 11 located between the backing layer and the skin contact layer. One end of the drainage tube 12 is attached to the backing layer 10 at a point adjacent to an opening 13 in the backing layer 10, such that the drainage tube 12 is in fluid communication with the interior of the dressing body 1, and in particular with the absorbent body 11.

The drainage tube 12 is formed of a knitted tube 14 that is sealed between two sheets of polyurethane film 15a,15b. The knitted tube 14 is knitted from a monofilament of a suitable synthetic polymer, for example polyester, polyamide, polyethylene, polypropylene or polybutylene terephthalate. The knitted tube 14 has an external diameter of approximately 6 mm. The sheets of polyurethane film 15a, 15b are heat-sealed to one another along the length of the knitted tube 14 on both sides of the knitted tube 14, so that the knitted tube 14 is surrounded by the sheets 15a,15b (see FIG. 2). The sheets 15a,15b extend beyond the end of the knitted tube 14 that is connected to the wound dressing, and terminate at this end in an integral circular tab 16 with a diameter that is significantly larger than that of the knitted tube 14. This circular tab 16 is adhered to the backing layer 10 using a suitable adhesive and forms an airtight seal around the knitted tube 14 and the opening 13 in the backing layer 10. A ring of a reinforcing material 17 is attached to the backing layer 10 around the opening 13 in the backing layer 10.

The end of the drainage tube 12 distal to the dressing body 1 is adapted for connection to a source of reduced pressure via a conventional screw fit connector 18. A short length of tubing 19 extends from the connector 18 and into the knitted tube 14 and is sealed between the sheets 15a,15b to form an airtight connection.

In use, the wound dressing 1 is placed over an exudating wound and the drainage tube 12 is connected to a source of reduced pressure. Exudate is absorbed from the wound into the dressing and sucked out through the tube. As the knitted tube 14 is flexible and resilient, it does not form kinks and can return to its original shape easily. As the tube 14 is also soft, it is comfortable if the patient lies on it and will not cause bedsores.

The invention claimed is:

1. A negative pressure wound therapy dressing comprising a dressing body and a drainage tube, wherein the drainage tube comprises a tube knitted or braided from a monofilament yarn and having a length, wherein an impermeable sheath including two separate sheets of an impermeable material sealed to one another along the length of the knitted or braided tube surrounds the knitted or braided tube such that the knitted or braided tube is sandwiched between the two separate sheets of the impermeable material, wherein the two sheets of the impermeable material are sealed to one another along the length of the knitted or braided tube without another layer being interposed between the knitted or braided tube and each of the two sheets of the impermeable material along a vertical plane passing through a center of the knitted or braided tube, wherein one end of the drainage tube has a tab integrally formed with the two sheets of impermeable material by which the drainage tube may be attached to the dressing body, wherein the knitted or braided tube extends along the length thereof from a first end to a second end arranged opposite the first end such that the knitted or braided tube has a constant diameter relative to an axis passing through the center of the knitted or braided tube, wherein a diameter of the tab is greater than the diameter of the knitted or braided tube, wherein the knitted or braided tube has a first tubular shape and the two sheets of impermeable material define a second tubular shape complementary to the first tubular shape of the knitted or braided tube, and wherein application of negative pressure in use of the negative pressure wound therapy dressing flattens the knitted or braided tube to facilitate conformance of the drainage tube to the skin of a patient.

2. The negative pressure wound therapy dressing according to claim 1 wherein the tube is a knitted tube.

3. The negative pressure wound therapy dressing according to claim 1 wherein the monofilament yarn is a polyester, polyamide, polyethylene, polypropylene, or polybutylene terephthalate monofilament yarn.

4. The negative pressure wound therapy dressing according to claim 1 wherein the knitted or braided tube has an external diameter of between 4 and 10 mm.

5. The negative pressure wound therapy dressing according to claim 1 wherein the impermeable sheath is adhered to the knitted or braided tube by heat sealing.

6. The negative pressure wound therapy dressing according to claim 1 wherein the impermeable sheath is a polyurethane sheath.

7. A drainage tube comprising a knitted or braided tube for use in medical applications, wherein the tube is knitted or braided from monofilament yarn and has a length of knitted or braided material extending from one end of the tube to another end of the tube arranged opposite the one end, wherein an impermeable sheath including two separate sheets of an impermeable material sealed to one another along the length of the knitted or braided tube surrounds the knitted or braided tube, wherein the two sheets of the impermeable material are sealed to one another at two seams that are circumferentially spaced 180 degrees from one another about an axis passing through a center of the knitted or braided tube, wherein the one end or the another end of the drainage tube has a tab integrally formed with the two sheets of impermeable material by which the drainage tube may be attached to a dressing, wherein the two sheets of the impermeable material are sealed to one another without another layer being interposed between the knitted or braided tube and each of the two sheets of the impermeable material along a vertical plane passing through the center of the knitted or braided tube, wherein the knitted or braided material acts as a filter that extends from the one end of the tube to the other end of the tube, wherein the knitted or braided tube extends along the length thereof from the one end of the tube to the other end of the tube such that the knitted or braided tube has a constant diameter relative to the axis, wherein a diameter of the tab is greater than the diameter of the knitted or braided tube, wherein the knitted or braided tube has a first tubular shape and the two sheets of impermeable material define a second tubular shape complementary to the first tubular shape of the knitted or braided tube, and wherein application of negative pressure using the drainage tube flattens the knitted or braided tube to facilitate conformance of the drainage tube to the skin of a patient.

8. The drainage tube according to claim 7 wherein the tube is knitted.

9. The drainage tube according to claim 7 wherein the monofilament yarn is a polyester, polyamide, polyethylene, polypropylene, or polybutylene terephthalate monofilament yarn.

10. The drainage tube according to claim 7 wherein the knitted or braided tube has an external diameter of between 5 and 8 mm.

11. The drainage tube according to claim 7 wherein the knitted or braided tube is sandwiched between the two sheets of the impermeable material.

12. The drainage tube according to claim 7 wherein the impermeable sheath is adhered to the knitted or braided tube by heat sealing.

13. The drainage tube according to claim 7 wherein the impermeable sheath is a polyurethane sheath.

14. A method of treating a wound comprising (a) applying a negative pressure wound therapy dressing according to claim 1 to a wound and (b) applying a negative pressure to the dressing via the drainage tube.

15. The negative pressure wound therapy dressing according to claim 1, wherein each of the two separate sheets of the impermeable material extends beyond an end of the knitted or braided tube to define the tab.

16. The negative pressure wound therapy dressing according to claim 15, wherein a surface area defined by the tab is larger than a surface area defined by the impermeable sheath.

17. The drainage tube according to claim 7, wherein each of the two separate sheets of the impermeable material extends beyond an end of the knitted or braided tube to define the tab.

18. The drainage tube according to claim 17, wherein a surface area defined by the tab is larger than a surface area defined by the impermeable sheath.

19. The negative pressure wound therapy dressing according to claim 1, wherein the two sheets of the impermeable material are sealed to one another at two seams that are circumferentially spaced 180 degrees from one another about the axis.

20. The drainage tube according to claim 7, wherein the two sheets of the impermeable material are sealed to one another along the length of the knitted or braided tube without another layer interposed between the two sheets of the impermeable material at one or more locations where the two sheets of the impermeable material are sealed to one another.

* * * * *